US00PP20648P3

(12) United States Plant Patent
Pierron-Darbonne

(10) Patent No.: US PP20,648 P3
(45) Date of Patent: Jan. 19, 2010

(54) STRAWBERRY PLANT NAMED 'DONNA'

(50) Latin Name: *Fragaria×ananassa*
Varietal Denomination: DONNA

(75) Inventor: Alexandre Pierron-Darbonne, Le Barp (FR)

(73) Assignee: Darbonne Pepiniere, Le Barp (FR)

( * ) Notice: Subject to any disclaimer, the term of this patent is extended or adjusted under 35 U.S.C. 154(b) by 211 days.

(21) Appl. No.: 11/825,250

(22) Filed: Jul. 3, 2007

(65) Prior Publication Data

US 2008/0271215 P1 Oct. 30, 2008

(30) Foreign Application Priority Data

Jul. 6, 2006 (EP) ..... 2006/1482

(51) Int. Cl.
*A01H 5/00* (2006.01)

(52) U.S. Cl. ..... Plt./208

(58) Field of Classification Search ..... Plt./208, Plt./209

See application file for complete search history.

*Primary Examiner*—Kent L Bell
(74) *Attorney, Agent, or Firm*—Christie, Parker & Hale, LLP.

(57) ABSTRACT

The present invention relates to a new and distinct strawberry variety. The varietal denomination of the new variety is 'DONNA'. Among the characteristics which appear to distinguish the new variety from other varieties are a combination of traits which include inflorescence that appears level with to above the foliage and abundant production of red colored, conical to wedged shaped, firm fruit, and medium fruit size.

6 Drawing Sheets

Botanical classification: *Fragaria×ananassa* 'DONNA'.

Varietal denomination: The new plant has the varietal denomination 'DONNA'.

BACKGROUND OF THE INVENTION

The present invention relates to a new and distinct cultivar of strawberry, botanically known as *Fragaria×ananassa* and hereinafter referred to by the cultivar name 'DONNA'.

The new variety of strawberry was created in a breeding program by crossing two parents; in particular, by crossing as seed parent an undistributed strawberry parent designated 98.05.17 (unpatented) and as pollen parent an undistributed strawberry parent designated 98.16.34 (unpatented). Both parental varieties are proprietary and have not been commercialized.

The new variety was discovered in a controlled breeding program of *Fragaria×ananassa* and differs from its parents and other known cultivars of *Fragaria×ananassa* by the following characteristics in combination:

1. The new variety of strawberry differs from its seed parent, designed 98.05.17 (unpatented), in the shape, color of fruits and the color of the stolons. The new strawberry variety is more tolerant to *Oidium* than the seed parent; and
2. The new variety of strawberry differs from its pollen parent, designated 98.16.34 (unpatented), in the shape of fruit, the firmness of fruit and the shape of incisions of margin of the terminal leaflet.

SUMMARY OF THE INVENTION

The cultivar 'DONNA' has not been observed under all possible environmental conditions. The phenotype may vary somewhat with variations in environment such as temperature, light intensity, nutrition and water status without, however, any variance in genotype.

The following traits have been repeatedly observed and are determined to be unique characteristics of 'DONNA'. These characteristics in combination distinguish 'DONNA' as a new and distinct cultivar:

1. inflorescence that appears level with to above the foliage;
2. abundant production of red colored, conical to wedged shaped, firm fruit of medium size.

The resulting seedling of the new variety was grown and asexually propagated by runners in Le Barp, Gironde, France 0,46° W., 44N., 150 feet elevation. Clones of the new variety were further asexually propagated and extensively tested. This propagation and testing has demostrated that the combination of traits disclosed herein which characterize the new variety are fixed and retained true to type through successive generations of asexual reproduction.

COMPARISON WITH OTHER CULTIVARS

The new variety is closest to the variety 'GARIGUETTE' (unpatented), but is distinguished therefrom by the following characteristics possessed by 'DONNA' which are different than, or not possessed by, 'DONNA' (unpatented):

1. 'GARIGUETTE' (unpatented) shows a leaf color of upperside (R.H.S. green group near 139 B to 143B) less dark than 'DONNA' (R.H.S. green group near 139 A to 143 A). 'GARIGUETTE' (unpatented) shows a leaf color of underside (R.H.S. green group near 138 B to 138 A) less dark than 'DONNA' (R.H.S. green group near 137 B to 137 A).
2. 'GARIGUETTE' (unpatented) exhibits a acute shape of base of terminal leaflet than 'DONNA' exhibits a rounded shape.
3. 'GARIGUETTE' shows a size of calyx relative to corolla larger, whereas 'DONNA' shows a same size of calyx relative to corolla.

4. The fruit size of 'GARIGUETTE' (unpatented) is shorter of 'DONNA'.
5. 'GARIGUETTE' (unpatented) shows a red fruit color (R.H.S. red group near 41B to 41 A), whereas in 'DONNA' it is an red fruit color (R.H.S. red group near 43A to 43B) with a stronger glossiness.
6. The predominant shape of fruits of 'GARIGUETTE' (unpatented) is bi-conical, whereas in 'DONNA' it is conical to wedged.
7. Fruit of the 'GARIGUETTE' (unpatented) exhibits an attitude of the calyx segments more reflexed than 'DONNA'.
8. Band without achenes in the fruit of 'GARIGUETTE' (unpatented) is broad to very broad than in 'DONNA' it is narrow.
9. 'GARIGUETTE' shows less firmness fruit than 'DONNA' fruit.

BRIEF DESCRIPTION OF THE DRAWINGS

The accompanying illustrations show a specimen of the new cultivar in a photographic illustration as true to color as is reasonably possible to make in an illustration of this character. Color values in the illustrations may differ slightly from the color values cited in the detailed botanical description, which accurately describes the actual colors of the new Strawberry.

The plants depicted in the drawings were planted Jul. 19, 2005 in Le Barp, Gironde, France 0,46° W., 44N., 150 feet elevation. Drawings were taken May, 2006 (about May 15, 2006): minimum temperature about 14 to 16° Centigrade, maximun temperature about 25 to 28° Centigrade.

DETAILED DESCRIPTION OF THE INVENTION

Figure 1:
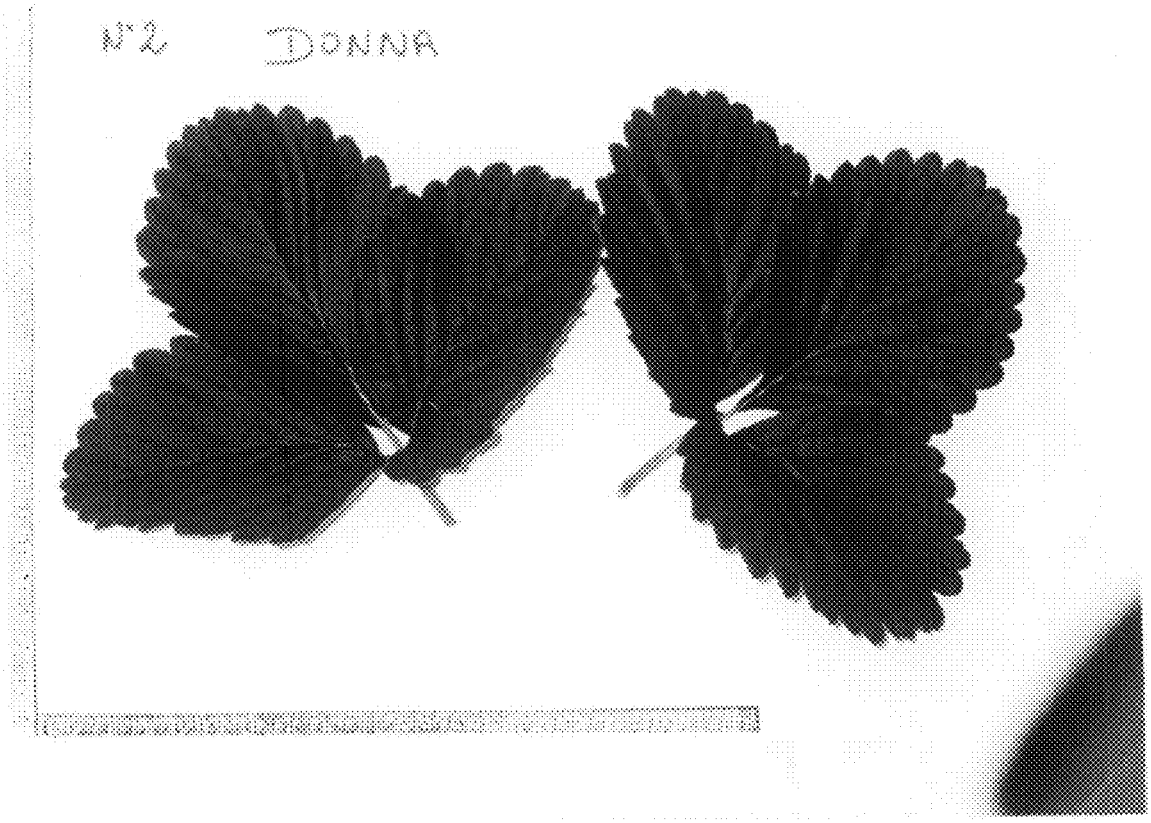
FIG. 1 the top of a complete leaf of the new variety, designated 'DONNA' (unpatented).
Figure 2:
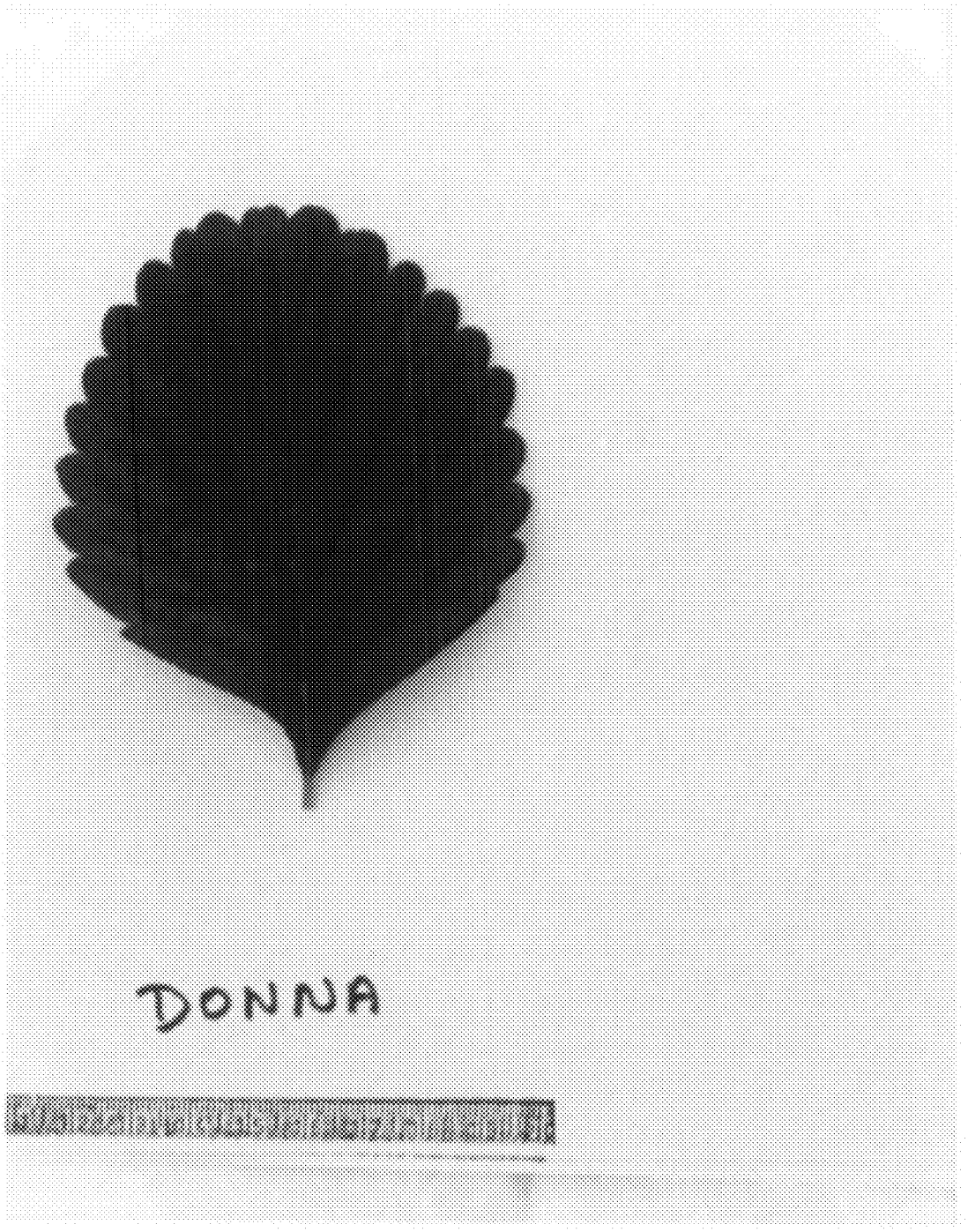
FIG. 2 shows the color of upper side of a typical terminal leaflet of the new variety (designated 'DONNA') (R.H.S. green group near 139 A to 143 A).
Figure 3:
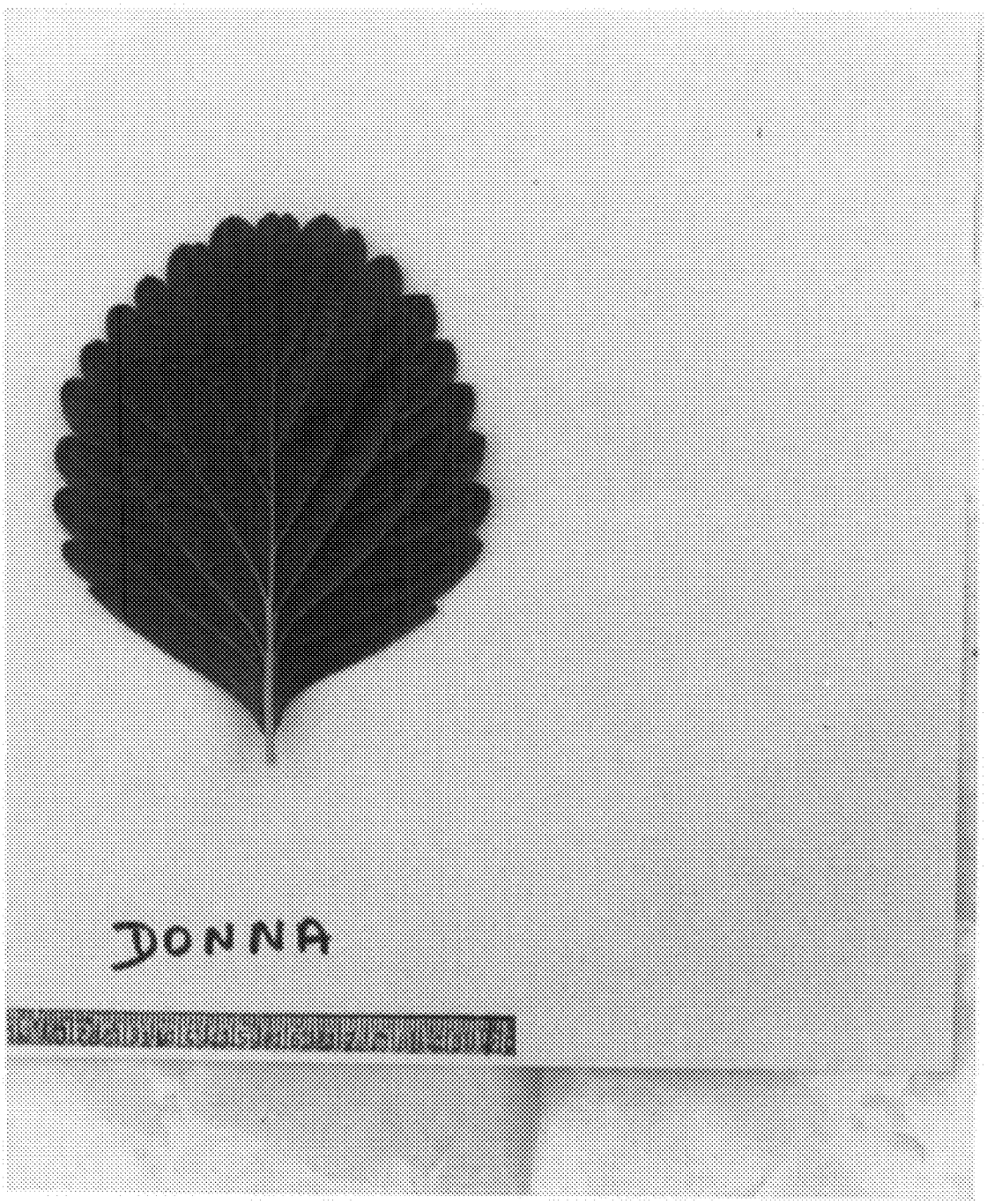
FIG. 3 shows the undersurface of a typical terminal leaflet of the new variety (designated 'DONNA') with a shape of base rounded.
Figure 4:
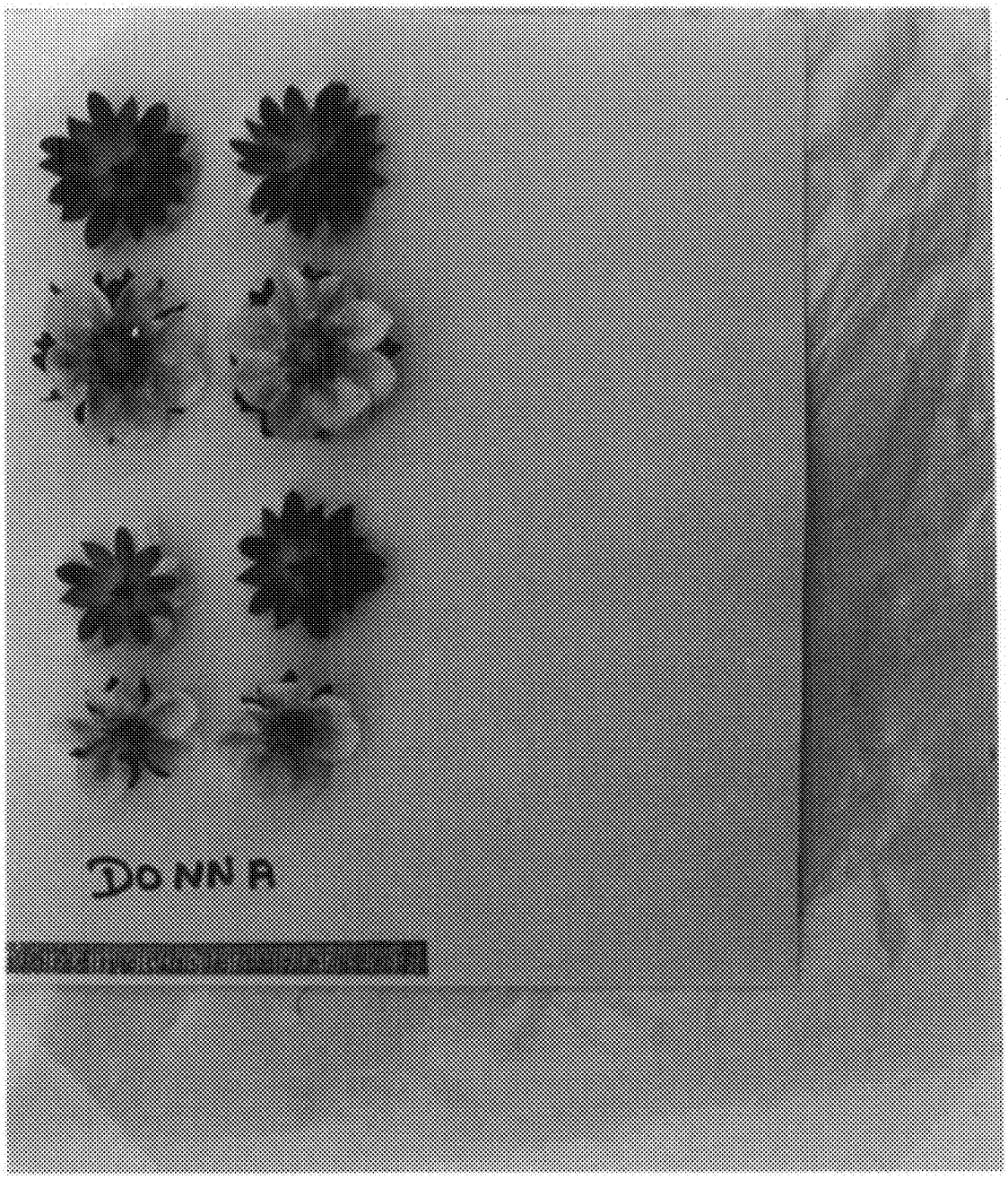
FIG. 4 shows the flower and reproductive organs of the new variety (designated 'DONNA').
Figure 5:
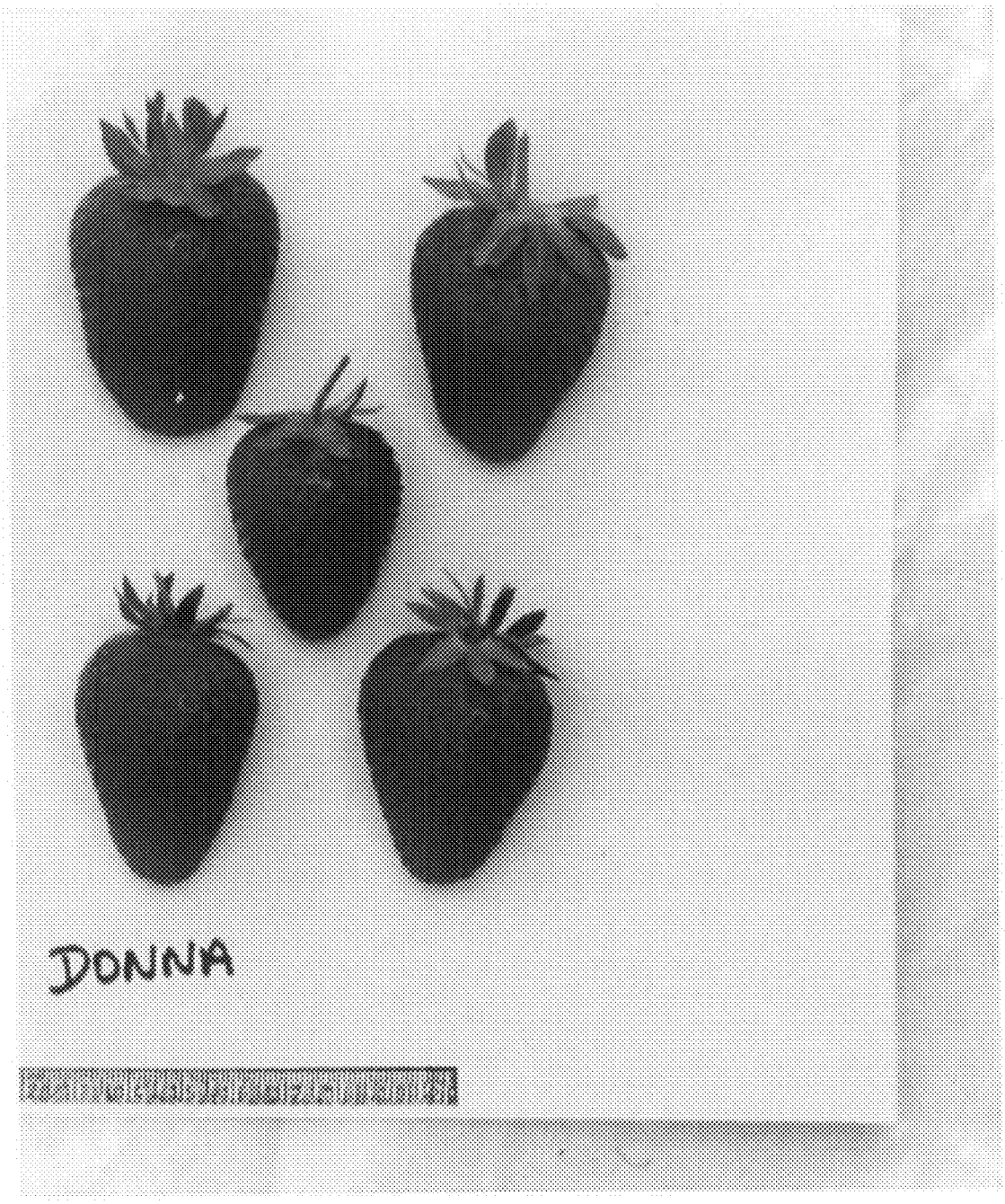
FIGS. 5 and 6 show typical fruit of the new variety (designated 'DONNA') whole, sliced and in cross section, illustrating the typical conical to wedged shape and flesh coloration, conspicuous core and core cavity, strong glossiness, red fruit color (R.H.S. red group near 43 A to 43 B) and a narrow band without achenes.
Figure 6:
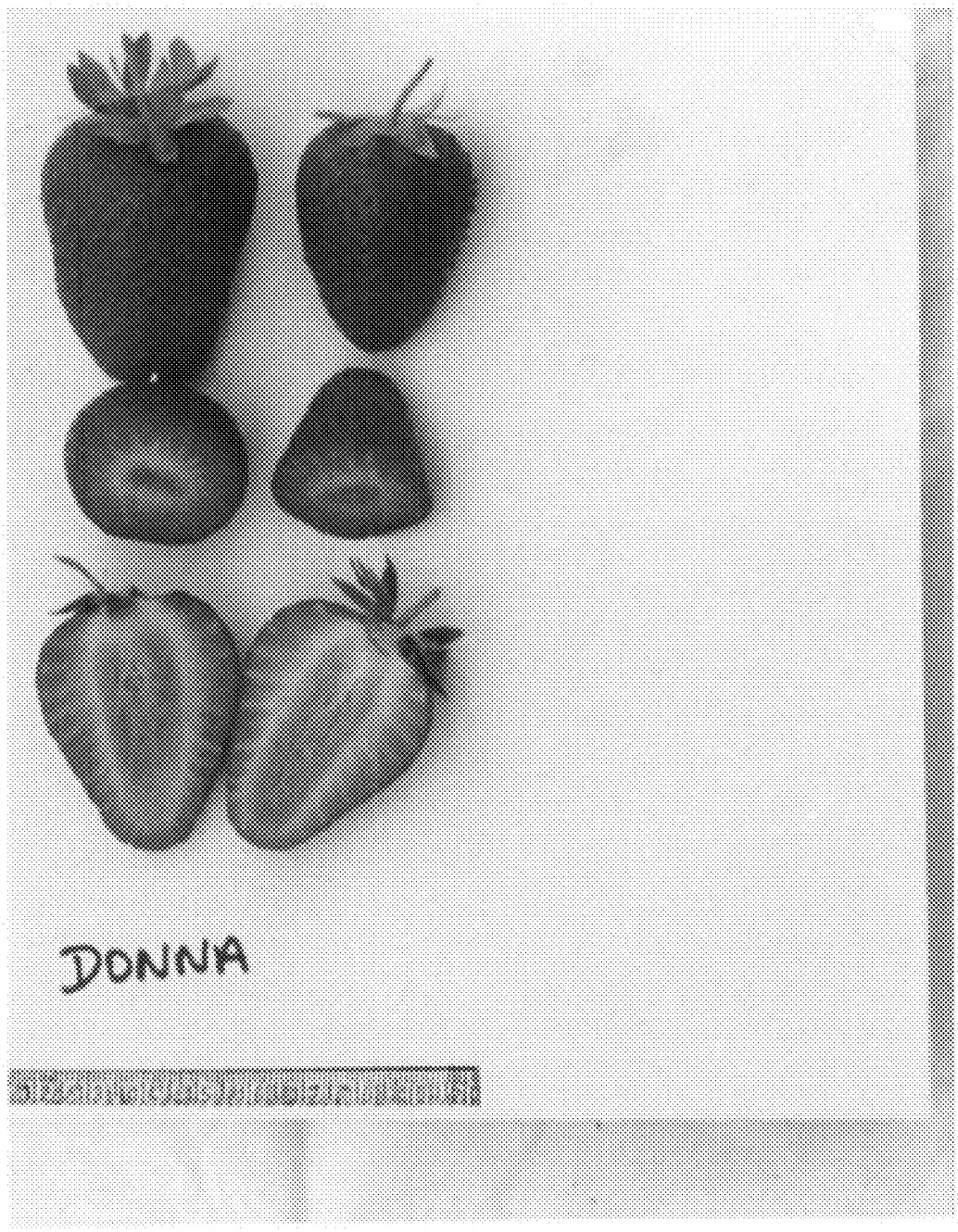

'DONNA' has not been observed under all possible environmental, cultural and light conditions. The following detailed description of the new variety is based upon observations taken of plants and fruits grown "underglass", i.e. undertunnel, in Le Barp, Gironde, France 0,46° W., 44N., 150 feet elevation.

The following description is in accordance with UPOV terminology and the color teminology herein is in accordance with The Royal Horticultural Society Colour Chart (R.H.S.C.C.). The color descriptions and other phenotypical descriptions may deviate from the stated values and descriptions depending upon variation in environmental, seasonal, climatic and cultural conditions.

GENERAL

'DONNA' is a partially remontat variety that needs an induction to flowering by chilling, such as occurs at nursery (fresh plant) or with cold storage (referred to as a frigo plant). Usually a short time is sufficient. 'DONNA' is self-fertile. It produces large quantity of pollen throughout the seasons and pollination is generally good as there are very few malformed fruit.

Classification:

*Botanical.*—*Fragaria×ananassa* 'DONNA'.

*Parentage.*—Female or Seed Parent: *Fragaria×ananassa* 98.05.17 (unpatented). Male or Pollen Parent: *Fragaria×ananassa* 98.16.34 (Unpatented).

*Propagation.*—By runners.

Plant:

*Size.*—Height: Approximately 24 cm. Diameter/Spread: Approximately 26/28 cm.

*Form and growth habit.*—Flat globose.

*Density.*—Medium.

*Vigor.*—Medium to Strong.

Stolons:

*Number.*—Many, about 15 to 20.

*Thickness.*—Medium, about 2.6 mm.

*Color.*—Yellow-green Group near 145A.

*Length.*—About 40 cm.

Leaf:

*Shape.*—Cordate. Apex: Acute. Base: Cordate.

*Leaf size.*—Approximately 11 cm long and 14 cm wide.

*Cross-section.*—Slightly concave.

*Aspect.*—Weak undulate or blistering.

*Coloration.*—Upper side: Green Group near 139A to 143A Under side: Green Group near 137B to 137A.

*Number of leaflets.*—Sometimes more than 3.

*Petioles.*—Size: Approximately 25 cm in length Hairs: Positioned Outwards Diameter: About 2.5 mm Length: About 7 mm Diameter: About 2–2.5 mm Coloration: Green Group near 138D to 142C Leaf Stem Color: Green Group near 145A. Leaf Stem Color: Green Group near 145A.

*Leaf stem Length.*—About 25 cm.

*Terminal leaflet characteristics.*—Lenget/Width Ratio: Equal Length: 7.5 cm Width: 7.5 cm Shape of Base: Rounded Shape of Teeth: Rounded.

*Stipules.*—Anthocyanin Coloration: Strong Color: Greyed-Red Group near 179B.

Inflorescence:

*Time from bloom to fruit.*—40 to 45 days.

*Position.*—Level with foliage to above.

*Size.*—Same size.

*Size of calyx relative to corolla.*—Medium.

*Arrangement of petals.*—Overlapping.

*Flower height.*—About 2.8 to 3.1 cm.

*Flower diameter* (*primary*).—Approximately 2.5–3.0 cm.

*Flower diameter* (*secondary*).—Approximately 2.0–2.5 cm.

*Fragrance.*—None noted.

*Petals.*—Number/Arrangement: About 5 to 8 overlapping petals Length/Width Ratio: Equal Shape: Almost rounded Length: 12–13 mm Width: 12–13 mm Apex: Rounded. Base: Almost rounded Coloration: Upper side: White group near 155B to 155D Under side: White group near 155B to 155D.

*Sepals.*—Number: About 10 Shape: Lanceolate Length: 10 mm Diameter: About 3–4 mm Apex: Acuminate Base: Flat Coloration: Upper side: Green Group near 143C to 143B Under side: Green Group near 138C to 138B.

*Buds.*—Length: About 14–15 mm Diameter: About 12–13 mm Coloration: Yellow-Green Group near 145C to 145B.

Reproductive organs:

*Stamens.*—Number: Numerous Stamen Length: Approximately 3 to 4 mm Color: Yellow-Green Group near 150C to 150D.

*Anthers.*—Size: Average Color: Yellow Orange Group near 15A and darkening with maturity Length: About 2 mm Width: About 1 mm.

*Pollen.*—Amount: Fertil & Abundant Color: Yellow Orange Group near 14B to 15B.

*Pistils.*—Number: Numerous Size: Average Color: Yellow Group near 12B Length: About 1 mm.

Fruit:

*Truss attitude.*—Semi-erect.

*Ratio of length/maximum width.*—Longer than broad.

*Color.*—Red Group near 43B to 43A.

*Peduncle color.*—Yellow-Green Group near 145A.

*Penduncle size.*—Length: About 70 mm Diameter: About 2 mm.

*Predominant shape.*—Conical to wedged.

*Primary fruit.*—Length: About 5.0 to 6.0 cm Width: About 3.5 to 4.5 cm.

*Secondary fruit.*—Length: About 3.5 to 4.0 cm Width: About 2.5 to 3.5 cm.

*Difference in primary secondary shape.*—Moderate.

*Band without achenes.*—Narrow.

*Color of achenes.*—Yellow-Green Group near 1B.

*Uneveness of surface.*—Weak to very weak.

*Insertion of achenes.*—Level with surface.

*Insertion of calyx.*—Level with fruit.

*Pose of calyx segments.*—Reflexed.

*Size of calyx in relation fruit diameter.*—Smaller to same size.

*Adherence of calyx.*—Strong.

*Glossiness.*—Strong.

*Flesh.*—Firmness: Firm Color of flesh: Orange Red Group near 34C to 34A Distribution of red color of flesh: Marginal and central, Uneven Hollow center: Weakly expressed Weight: About 20–21 grams Sweetness: 7.2% Brix Acidity: Anhydride Citric 0.97%.

Growth characteristics:

*Time of flowering* (50% *of plants at first flower*).—Early.

*Time of ripening* (50% *of plants with ripe fruits*).—Early.

*Type of bearing.*—Patially remontant.

*Chilling.*—Weak.

*Planting date.*—Jul. 15 to 25, 2005.

10% *flowering.*—Mar. 10, 2006.

*First mature fruits.*—Apr. 5, 2006.

*Maturity* (15–20 *gms/plant*).—Apr. 20, 2006.

Ripening characteristics: After planting as aforesaid, plants are grown in raised beds undertunnel (small tunnel with small holes in plastic walls). Water and fertilizer were applied through drip irrigation. Time of ripening (50% of plants with ripe fruit) is about Apr. 10, 2006. First mature fruit is about Apr. 5, 2006 and maturity (15–20 gms/plant) is about Apr. 20, 2006.

Storage qualities: 'DONNA' fruit maintain their quality characteristics when kept in a chamber at temperatures of about 2° C. for 48 hours. The fruit's color and glossiness remain substantially the same.

Pests/diseases: Tolerant to *Oidium*, no particular sensisivity to any disease or parasite observed.

Fruit production comparison: Comparison with 'GARIGUETTE' (unpatented): The new variety is compared with 'GARIGUETTE'.

TABLE 1

Accumulated production of 1st quality fruit (g/plant)

| Variety | 31 April | 10 May | 24 May | 1st/2nd Quality Fruit | Total (g/fruit) | |
|---|---|---|---|---|---|---|
| CLERY | 236 | 430 | 836 | 836 + 44 | 880 | 24-17 |
| GARIGUETTE | 135 | 407 | 748 | 748 + 172 | 920 | 18-11 |
| DONNA | 234 | 480 | 1032 | 1032 + 128 | 1160 | 21-14 |

TABLE 2

Production total of First Quality Fruit and Second Quality Fruit in g/plant

| Variety | 1st quality | 2nd quality | Total | % 2nd Q |
|---|---|---|---|---|
| CLERY | 836 | 44 | 880 | 5 |
| GARIGUETTE | 748 | 172 | 920 | 23 |
| DONNA | 1032 | 128 | 1160 | 12 |

TABLE 3

Weight (g/Fruit) at two dates: 31 April and 24 May

| WEIGHT (g/fruit) | 31 April | 24 May |
|---|---|---|
| CLERY | 24 | 21 |
| GARIGUETTE | 18 | 16 |
| DONNA | 21 | 20 |

(WEIGHT is shown as the average weight per fruit in First Quality Fruits.)

General: The growing period in Le Barp, Gironde, France, where the observations were made, is between about February 20 and May 30 of each year, with a maximum production at about between April 25 and May 15. 'DONNA' is a partially remontant variety that benefits from induction to flowering by chilling, usually 700 to 900 hours are sufficient, preferably at temperatures of 7° C. or less. Normally, the minimum number of hours are acumulated in the field during several days.

What is claimed is:

1. A new *Fragaria×ananassa* plant named 'DONNA', substantially as shown and described.

* * * * *